United States Patent [19]

Hiroi et al.

[11] Patent Number: 5,110,964
[45] Date of Patent: May 5, 1992

[54] PROCESS FOR PRODUCING FERROCENOYL DERIVATIVES

[75] Inventors: Yoshio Hiroi; Seiichiro Yokoyama, both of Chiba, Japan

[73] Assignee: Idemitsu Kosan Co., Ltd., Tokyo, Japan

[21] Appl. No.: 623,642

[22] PCT Filed: May 10, 1990

[86] PCT No.: PCT/JP90/00595

§ 371 Date: Dec. 12, 1990

§ 102(e) Date: Dec. 12, 1990

[87] PCT Pub. No.: WO90/13554

PCT Pub. Date: Nov. 15, 1990

[30] Foreign Application Priority Data

May 12, 1989 [JP] Japan ............................. 1-117482
Jul. 7, 1989 [JP] Japan ............................. 1-174047

[51] Int. Cl.$^5$ .................................................. C07F 17/02
[52] U.S. Cl. ........................................ 556/143; 556/138; 556/140; 556/144
[58] Field of Search ................ 556/138, 140, 143, 144

[56] References Cited

U.S. PATENT DOCUMENTS

| 3,960,911 | 6/1976 | Suschitzky et al. | 556/143 |
| 3,989,731 | 11/1976 | Talbot | 556/143 |
| 5,041,582 | 8/1991 | Eida et al. | 556/143 |

OTHER PUBLICATIONS

Herve' des Abbayes & Rene' Dabard, Ste're'o-chimie dans 1 a Se'rie des ferrocenyl-cyclohe'xenones α et β disubstitue'es, Compt. Rend. Acad. Sci. t. 276, Jun. 1973, Ser. C, pp. 1763 to 1766.

Primary Examiner—Arthur C. Prescott
Attorney, Agent, or Firm—Frishauf, Holtz, Goodman & Woodward

[57] ABSTRACT

Disclosed is a process for producing a ferrocenoyl derivative comprising the reaction of ferrocene derivative with monocarboxylic acid or dicarboxylic acid in the presence of a catalyst.

The ferrocenoyl derivative obtained by said process is very useful as the intermediate product for various functional materials, among all, for the micelle forming agents (surfactants) in so-called Micellar Disruption Method or the intermediate product of it.

6 Claims, 16 Drawing Sheets

PROCESS FOR PRODUCING FERROCENOYL DERIVATIVES

TECHNICAL FIELD

The present invention relates to a process for producing ferrocenoyl derivatives, more particularly it is concerned with a process for an efficient production of ferrocenoyl derivatives by reacting a ferrocene derivative with a monocarboxylic acid or a dicarboxylic acid in the presence of a catalyst.

BACKGROUND ART

Generally, ferrocenoyl derivatives are very useful as the intermediate material for producing highly active functional materials having a ferrocene skeleton, such as functional polymers, LB films, surfactants, charge-transfer complexes, ion sensors, masking reagents, and coupling agents.

Such ferrocenoyl derivatives have heretofore been produced according to a process in which a carboxylic acid is converted into acid halide and then the resulting acid halide is reacted with a ferrocene derivative in the presence of a Lewis acid catalyst such as aluminum chloride.

That process, however, will involve byproducts in which each of two five-membered rings of ferrocene derivatives has been acylated. Accordingly, to inhibit such byproducts, the way of adding ferrocene derivatives must be selected. Moreover, when a compound containing halogen atom is used as the carboxylic acid, the reaction temperature should be controlled to be under 5° C., so as to inhibit dehalogenation reaction.

Further, the acylation reaction of ferrocene derivative with the use of catalysts such as polyphosphoric acid has been known (J. Am. Chem. Soc. 79,3290 (1957)). It is, however, an intramolecular reaction, and any intermolecular acylation of ferrocene derivatives which is required for selectivity has not been known.

Particularly, to produce a ferrocenoyl derivative having carboxyl group, a very complicated process has been required wherein one carboxylic acid of dicarboxylic acid is esterified by use of disproportionation reaction, then the other unreacted carboxylic acid is acid-halogenated, and the resulting product is reacted with ferrocene derivative under the condition of usual Friedel-Crafts reaction, to obtain ferrocenoyl derivative carboxylate, and after that, said ester is hydrolyzed (PCT Int. Appln. Laid-Open WO89/01939).

Above process, however, required so many steps and complicated operations but the yield was insufficient that it was not suitable for practical use.

DISCLOSURE OF INVENTION

Under these circumstances, the present inventors had earnestly repeated investigations to overcome the above defects of the conventional process described above, and to produce ferrocenoyl derivatives efficiently with simple steps.

As the result, it was found that the object can be attained by reacting directly a ferrocene derivative with monocarboxylic acid or dicarboxylic acid in the presence of a catalyst comprising phosphoric acid or its derivative. The present invention has been accomplished based on such findings.

The present invention provides a process for producing ferrocenoyl derivatives which is characterized by reacting a ferrocene derivative with a monocarboxylic acid or a dicarboxylic acid in the presence of a catalyst.

THE MOST PREFERRED EMBODIMENT TO CARRY OUT THE INVENTION

Figure 1:
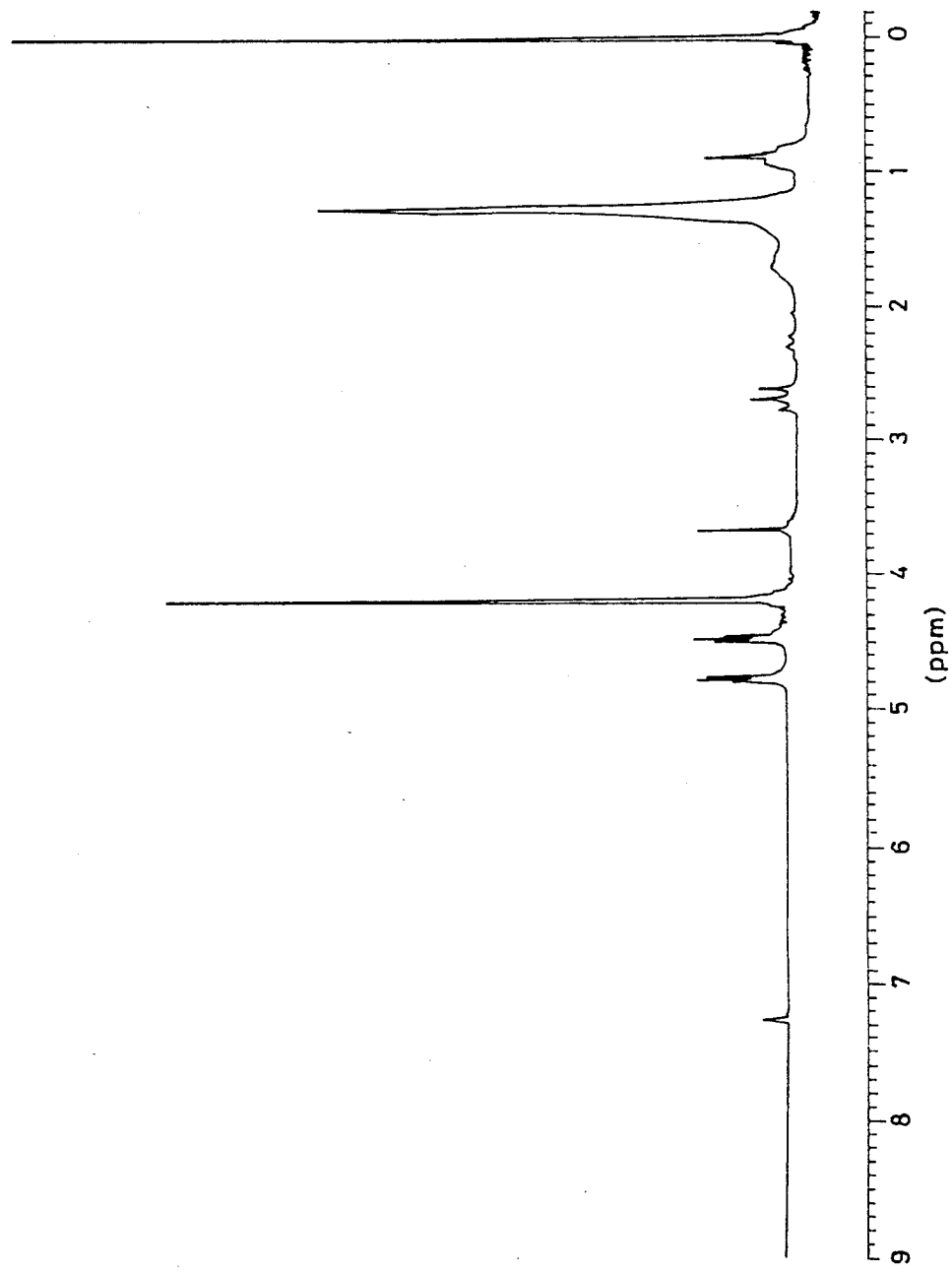
FIG. 1 to FIG. 16 show each $^1$H—NMR (proton nuclear magnetic resonance) spectrum of the ferrocenoyl derivative produced in Examples 1 to 16, respectively.

The present invention employs, as the reaction material, ferrocene derivative and monocarboxylic acid or dicarboxylic acid. Herein, as the ferrocene derivative, ferrocene and various substitution products thereof in a wide range are used. Said substituted ferrocenes are not critical, and include various ones in which various substituent groups may have been introduced into the ferrocene skeleton.

Said substituents of ferrocene may vary as long as they do not inhibit the proceeding of ordinary Friedel-Crafts reaction, and the positions and the numbers of said substituents are not specified as long as Friedel-Crafts reaction is not inhibited in proceeding. Preferred ferrocene derivatives are those represented by the general formula:

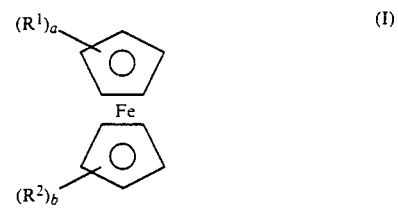

(wherein $R^1$ and $R^2$ are each a hydrogen atom, a methyl group, a methoxyl group, a hydroxyl group, an amino group, a dimethylamino group or a halogen atom, a indicates an integer of 1 to 4, and b indicates an integer of 1 to 5.)

On the other hand, monocarboxylic acid or dicarboxylic acid as another material for the process of the present invention can be selected appropriately according to the type of said ferrocene derivatives, the desired ferrocenoyl derivatives, or further, various reaction conditions. The main chain which constitutes said monocarboxylic acid or dicarboxylic acid is not critical, provided that it has at least one carbon atom, whether straight chain or branched chain, and the position of the carboxylic acid may vary in many embodiments including the terminal of the molecule.

Among them, preferred examples of said monocarboxylic acid are the compounds represented by the general formula:

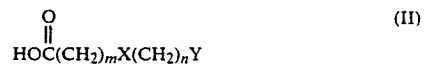

and similarly, preferred examples of the dicarboxylic acid are the compounds represented by the general formula:

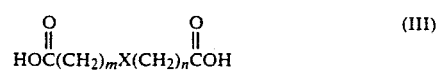

In the above general formula (II) and (III), X is

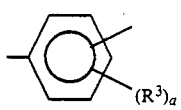

(R³ indicates a hydrogen atom, an alkyl group having 1 to 5 carbon atoms, an alkoxyl group having 1 to 5 carbon atoms, a hydroxyl group, an amino group, a di-methylamino group, an alkoxycarbonyl group having 1 to 5 carbon atoms or a halogen atom, and a is as defined above),

(R³ is as defined above),

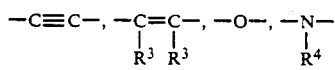

(R⁴ is a hydrogen atom or an alkyl group having 1 to 5 carbon atoms),

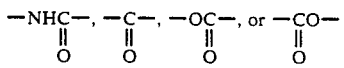

m and n are positive integers satisfying $0 \leq m+n$, and more particularly, positive integers satisfying $0 \leq m+n \leq 19$.

In general formula (II), Y indicates a hydrogen atom, a halogen atom or a nitrile group. Besides, in the above general formulae (II) and (III), those which have plural substituents X (for example, a compound in which plural phenylene groups, substituted phenylene groups, alkylidene groups and the like exist continuously or interposed by some methylene groups ($CH_2$)), or those in which X is a condensed polycyclic group such as naphthalene ring, and anthracene ring.

Further, when Y is other than a hydrogen atom, it can be protected in reaction, if necessary, by a protecting group usually used, and the protecting group can be separated away after the reaction.

The preferable examples of such monocarboxylic acids are fatty acids such as lauric acid, and stearic acid; halogenated fatty acids such as 11-bromoundecanoic acid, and 4-bromobutyric acid; cianide of fatty acids such as cyanoacetic acid; aromatic monocarboxylic acids such as p-chlorobenzoic acid, and p-cyanobenzoic acid; and also monoesters of dibasic acids such as monomethyl suberate, monoethyl sebacate, and monomethyl terephthalate.

Preferable examples of dicarboxylic acids are aliphatic dicarboxylic acids such as sebacic acid, adipic acid, glutaric acid, 3,3-dimethyl glutaric acid, hexadecane dicarboxylic acid, and undecane dicarboxylic acid; and aromatic dicarboxylic acids such as terephthalic acid.

In the process of the present invention, the above-described reaction of a ferrocene derivative with a monocarboxylic acid or a dicarboxylic acid proceeds in the presence of a catalyst. Therein as the catalyst, various ones can be used, but particularly preferable are the catalyst comprising phosphoric acid or its derivative. Said phosphoric acids or derivatives thereof include various ones, and can be selected appropriately. Specific examples of them are phosphoric acid, methaphosphoric acid, orthophosphoric acid, pyrophosphoric acid, polyphosphoric acid, phosphoric acid halide, phosphorus halide or mixtures thereof. Further in detail, phosphoric acids include 85% phosphoric acid, and 99% phosphoric acid; and phosphoric acid halides include $$POCl_3, \; ROPCl_2, \; \text{and} \; (RO)_2PCl;$$
$$\qquad \quad \; \overset{\|}{O} \qquad \qquad \overset{\|}{O}$$

and phosphorus halides include $PCl_3$, $PCl_5$, $RPCl_2$, and $R_2PCl$. Therein, R is a methyl group, an ethyl group, a n-propyl group, an iso-propyl group, a phenyl group and the like.

In the process of the present invention, besides the catalysts comprising phosphorus acid or its derivative, various acids such as hydrofluoric acid, and sulfuric acid can be used as the catalyst.

In the process of the present invention, the above reaction material is required only to be react in the presence of the catalyst as mentioned above, and the conditions therein are not particularly limited. The reaction proceeds in the absence of or presence of solvent, at any temperature either for cooling or heating, and under any pressure ranging from a reduced pressure to ordinary one or, further, higher one.

Following are more specific reaction conditions, for example, when a phosphoric acid-based catalyst such as phosphoric acid, methaphosphoric acid, orthophosphoric acid, pyrophosphoric acid, polyphosphoric acid or the mixture thereof is used as the catalyst.

The pressure should be in the range of a reduced pressure of 0.001 mmHg to ordinary pressure The temperature should be 0° to 300° C., preferably room temperature to 200° C., when monocarboxylic acid is used; and room temperature to 300° C., preferably 40° to 200° C. when dicarboxylic acid is used. The reaction period is 30 minutes to 24 hours, preferably 1 to 5 hours.

Under such conditions, the reaction proceeds in the absence of solvent or in the presence of an aprotic solvent such as halogen-based solvents including methylene chloride, chloroform, carbon tetrachloride, dichloroethylene, methylbromide, methylene bromide, and tribromomethane; ether-based solvents including diethylether, tetrahydrofuran (THF), dioxane, and di n-butylether; and solvents used for Friedel-Crafts reaction such as nitrobenzene, carbon disulfide, and nitromethane.

With respect to the ratio of the material and the catalyst, based on the amount of ferrocene derivative, it is preferred to use an equivalent to 5 times equivalent of monocarboxylic acid or dicarboxylic acid, 0.1 to 500 times equivalent of the above-mentioned phosphoric acid derivative-based catalyst when monocarboxylic acid is used, and 10 to 500 times equivalent of said catalyst when dicarboxylic acid is used.

When these materials and catalyst are added to the reaction system, all of them can be added at once, and it is also effective to add ferrocene derivative after the above phosphoric acid derivative-based catalyst and monocarboxylic acid or dicarboxylic acid are reacted.

The specific reaction conditions for the use of phosphoric acid derivative-based catalyst such as various phosphoric acid halides and phosphorus halides as the catalyst are as follows.

The pressure should be in the range from a reduced pressure of 0.001 mmHg to ordinary pressure, the temperature should be −20° to 200° C., preferably −5° to 100° C., and the reaction period should be 30 minutes to 10 hours, preferably 1 to 3 hours. Under these conditions, a base such as triethylamine, pyridine, and N,N-dimethylaminopyridine is added, and the reaction is made to proceed in the aprotic solvent as described before. With respect to the ratio in amount of the material and the catalyst, based on the ferrocene derivative, it is preferred to use one to 10 times equivalent of monocarboxylic acid, 0.1 to 10 times equivalent of the above-mentioned phosphoric acid derivative-based catalyst, and 0.1 to 10 times equivalent of a base when monocarboxylic acid is used. When dicarboxylic acid is used, 1 to 5 times equivalent of dicarboxylic acid, ½ to 3 times equivalent of above-described phosphoric acid derivative-based catalyst, and 1 to 10 times equivalent of bases.

When these materials and catalyst are added to the reaction system, all of them can be added at once, and it is also effective to add ferrocene derivative after the above phosphoric acid derivative-based catalyst and monocarboxylic acid or dicarboxylic acid are reacted.

The present invention is explained in greater detail with reference to the Examples and Comparative Examples as follows.

EXAMPLE 1

8.01 g of lauric acid was added to 100 ml of 85% phosphoric acid and 100 g of polyphosphoric acid, and heated at 180° C. for three hours while the pressure was reduced (1 mmHg) with the use of vacuum pump. After the mixture was cooled, 1.86 g of ferrocene and 20 ml of methylene chloride were added, and the resulting mixture was heat-refluxed at 50° C. for 9 hours. Then, the mixture was poured into water, and made to be basic with potassium hydroxide, and subjected to extraction with methylene chloride, and dried. The unreacted ferrocene was removed by a column chromatography, to obtain 3.20 g of undecanylferrocenyl ketone represented by the formula (A) in a yield of 87.0%. The proton nuclear magnetic resonance ($^1$H—NMR) spectrum of the product is shown in FIG. 1.

The result showed that the resulting product was the desired compound (undecanylferrocenyl ketone).

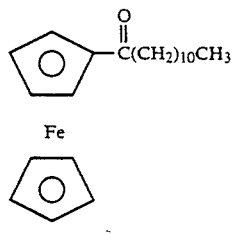
(A)

EXAMPLE 2

Figure 2:
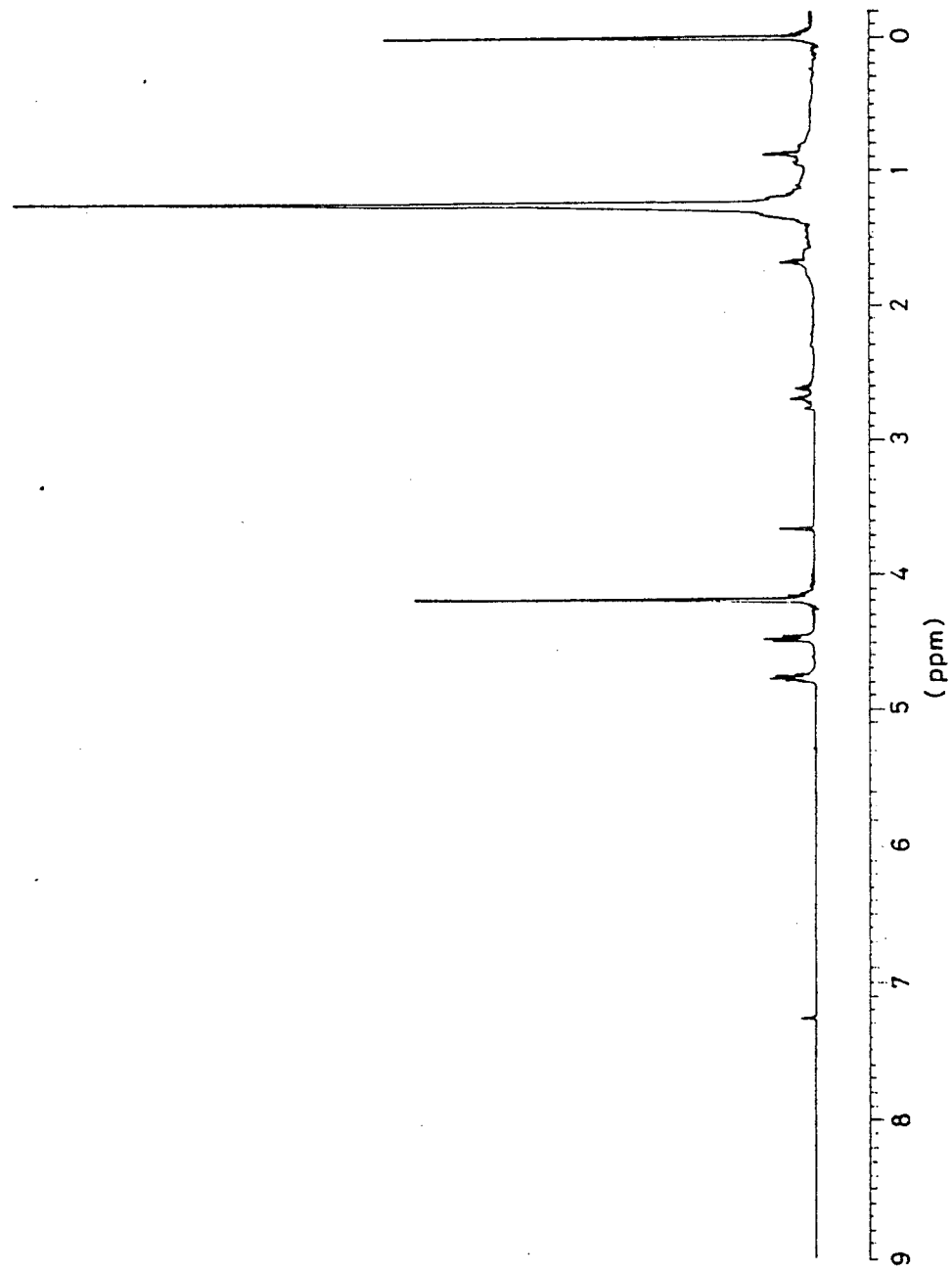

The procedure of Example 1 was repeated except that 100 g of pyrophosphoric acid was used in place of 85% phosphoric acid and polyphosphoric acid, 11.38 g of stearic acid was used in place of lauric acid, and the reaction was carried out under ordinary pressure, to obtain 3.12 g of ferrocenylheptadecanyl ketone represented by the formula (B), in a yield of 72.0%. The nuclear magnetic resonance ($^1$H—NMR) spectrum of the product is shown in FIG. 2. The result showed that the resulting product was the desired compound (ferrocenylheptadecanyl ketone).

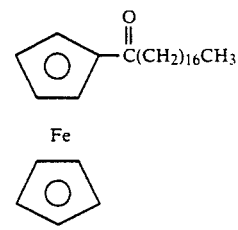
(B)

EXAMPLE 3

Figure 3:
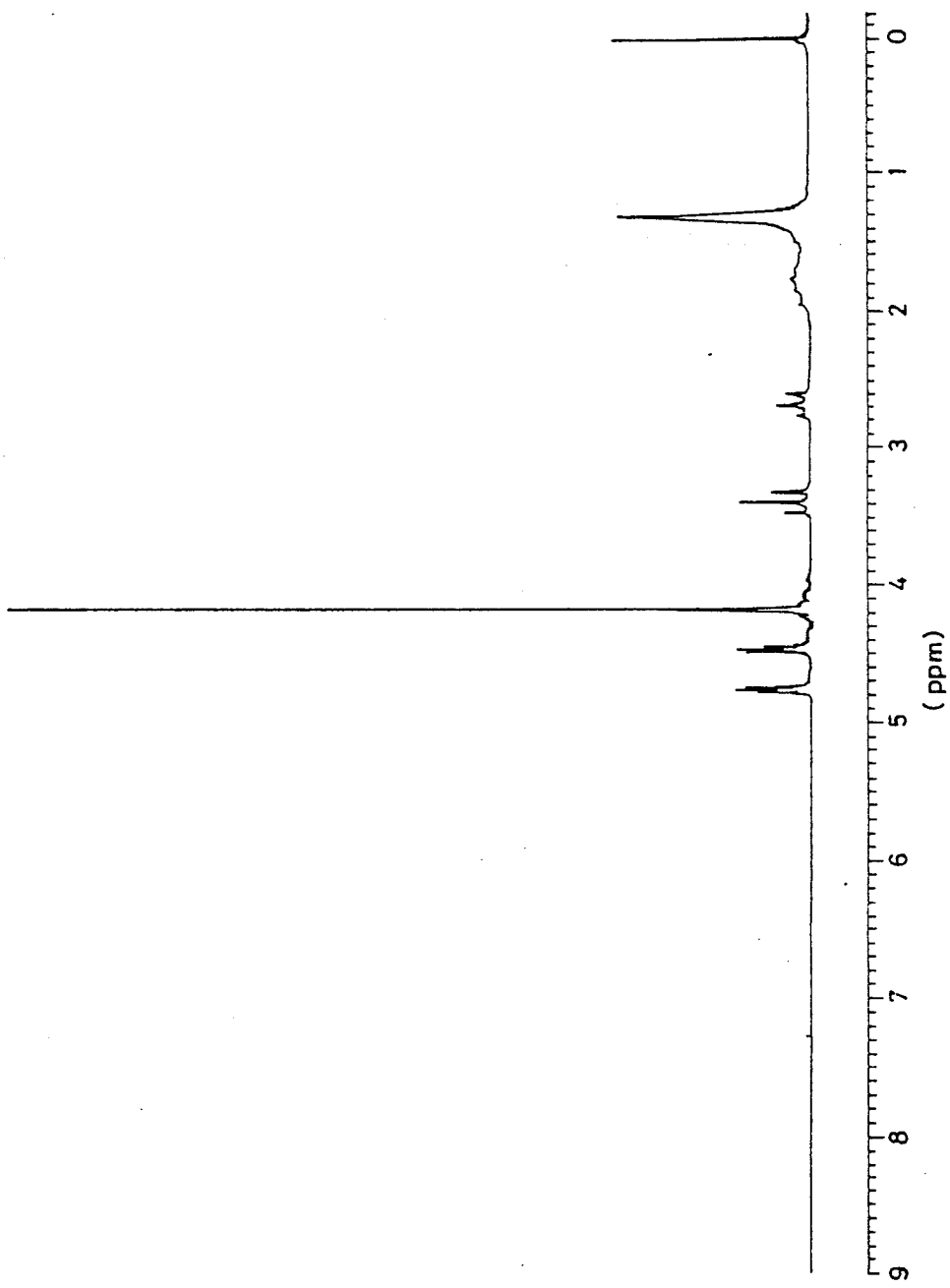

10.61 g of 11-bromoundecanoic acid, 1.86 g of ferrocene, and 50 g of pyrophosphoric acid were added and stirred while heating at 50° to 60 ° C. for 5 hours, and then poured into water, made to be basic with sodium hydroxide, subjected to extraction with methylene chloride, and dried. Then, the unreacted ferrocene was removed with column chromatography, to obtain 4.00 g of 10 -bromoundecanylferrocenyl ketone represented by the formula (C) in a yield of 92.3%. The proton nuclear magnetic resonance ($^1$H—NMR) spectrum of the product was shown in FIG. 3. The result showed that the resulting product was the desired compound (10-bromoundecanylferrocenyl ketone).

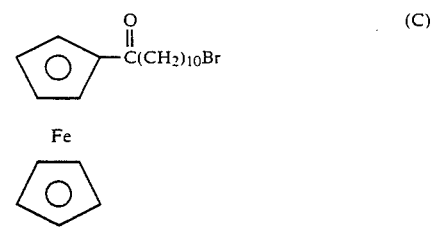
(C)

EXAMPLE 4

Figure 4:
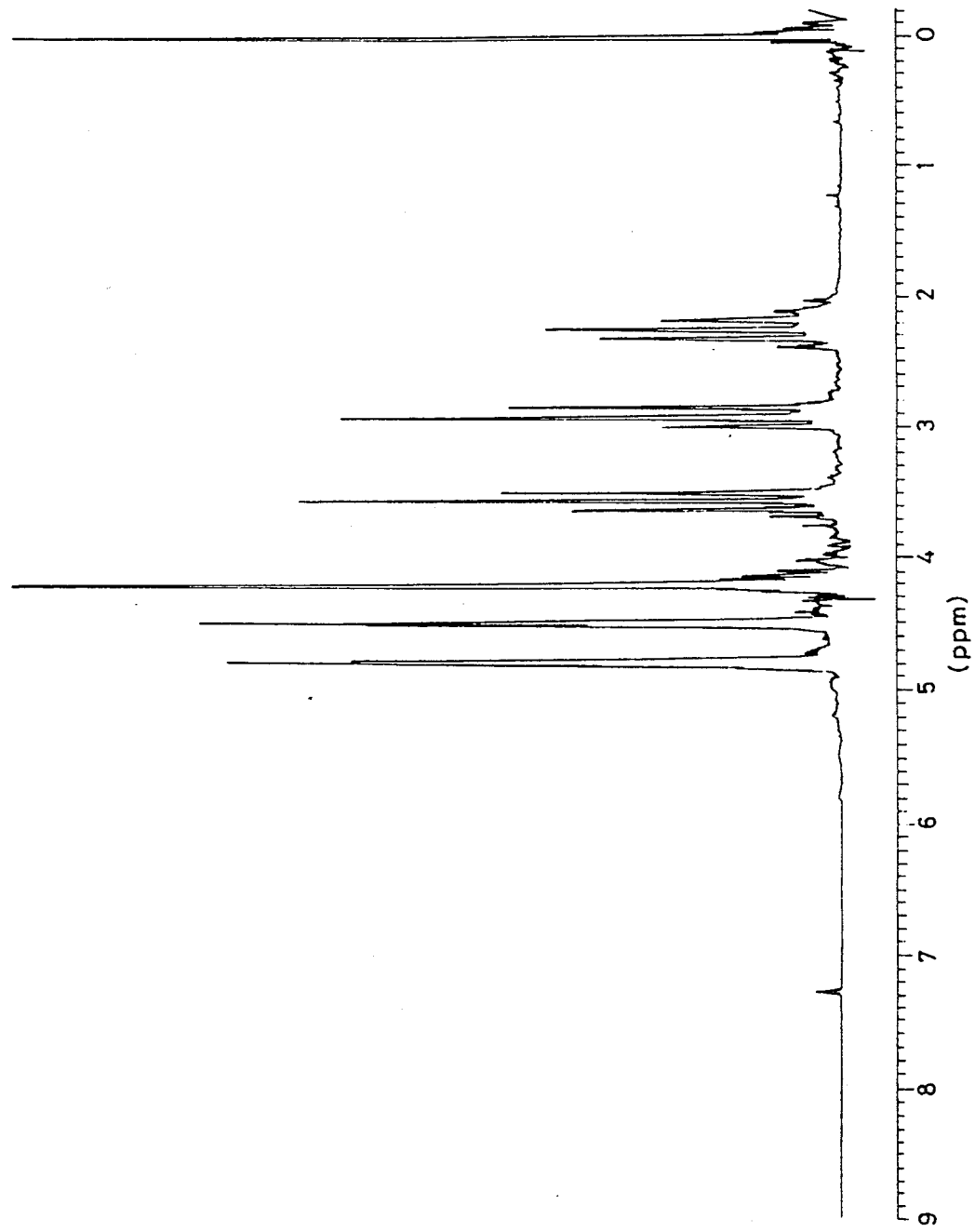

6.68 g of 4-bromobutyric acid, 1.86 g of ferrocene, 20 g of pyrophosphoric acid, 20 g of polyphosphoric acid, and 20 ml of di n-butylether were added and stirred while heating at 50° to 60° C. for 3 hours, then poured into water, made to be basic with sodium hydroxide, extracted with methylene chloride, and dried. The unreacted-ferrocene was removed with column chromatography, to obtain 2.75 g of 3-bromopropylferrocenyl ketone presented by the formula (D), in a yield of 82.0%. The proton nuclear magnetic resonance ($^1$H—NMR) spectrum of the product is shown in FIG. 4. The result showed that the resulting product was the desired product (3-bromopropylferrocenyl ketone).

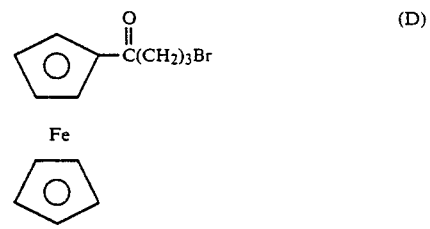
(D)

EXAMPLE 5

Figure 5:
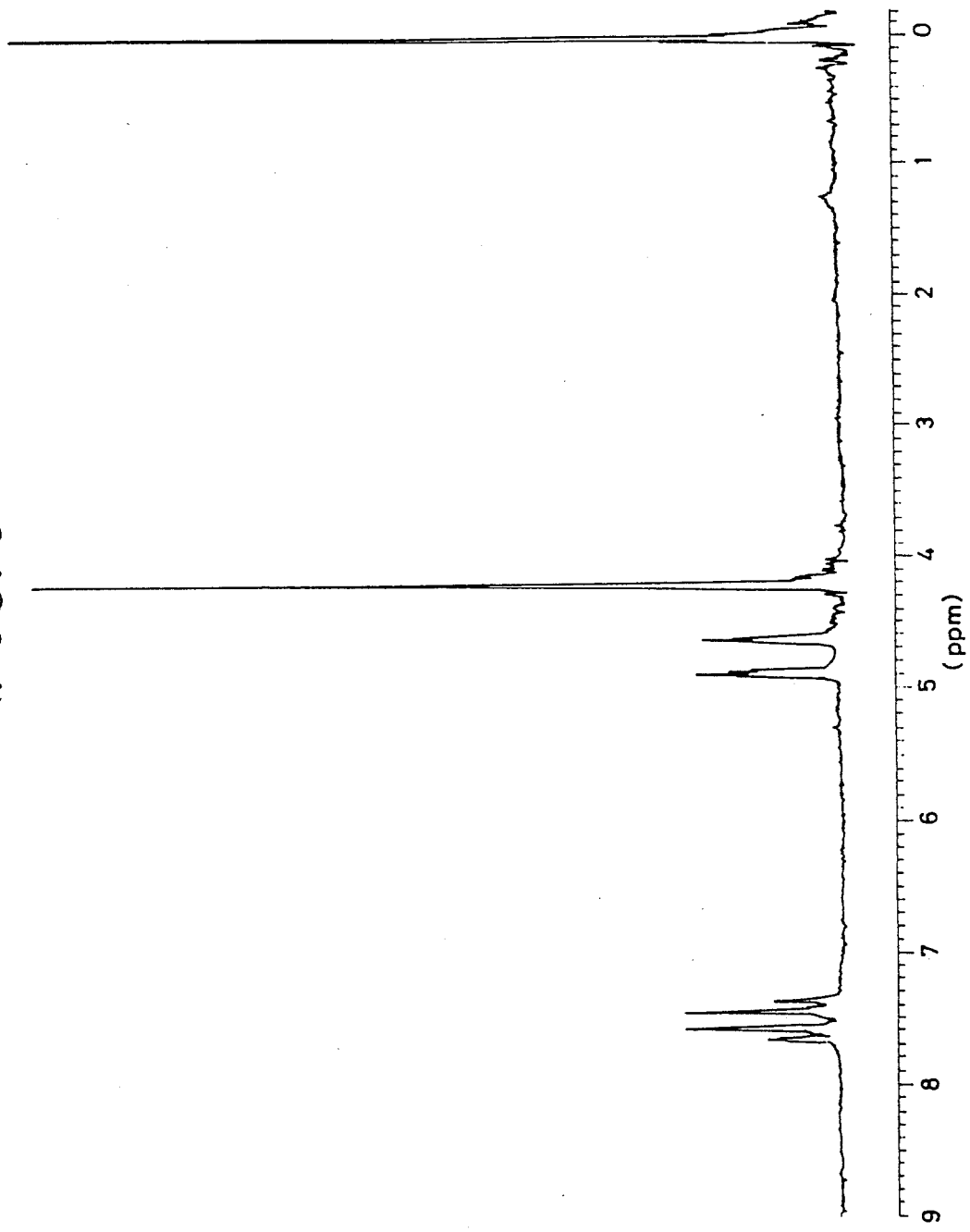

5.30 of p-chlorobenzoic acid, 1.0 ml of triethylamine, and 2 ml of phosphorus oxychloride were added and stirred at 0° C. for 30 minutes with 40 ml of methylene chloride, and 60 ml of pyrophosphoric acid and 6.0 g of ferrocene were added. The resulting mixture was heat-refluxed, then poured into water, and made to be basic with sodium hydroxide, subjected to extraction with methylene chloride, and dried. Subsequently, the unreacted ferrocene was removed with column chromatography, to obtain 6.16 g of p-chlorophenylferrocenyl ketone represented by the formula (E), in a yield of 61.0%. The proton nuclear magnetic resonance ($^1$H—NMR) spectrum of the product is shown in FIG. 5. The result showed that the resulting product was the desired compound (p-chlorophenylferrocenyl ketone).

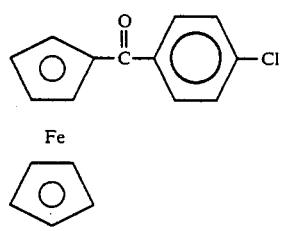

(E)

EXAMPLE 6

Figure 6:
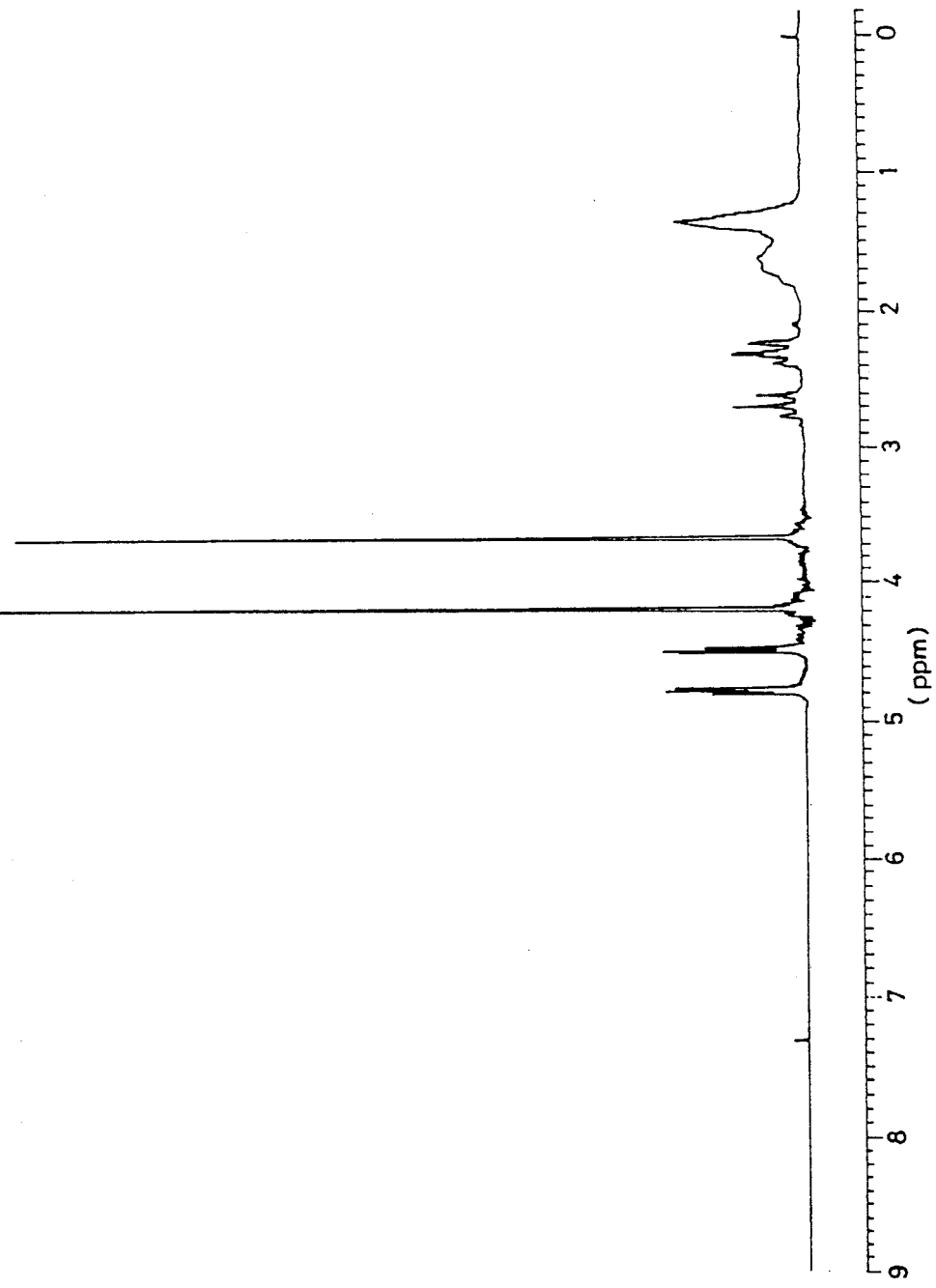

The procedure of Example 5 was repeated except that 6.37 g of monomethyl suberate in place of p-chlorobenzoic acid, 0.57 g of diethyl chlorophosphate in place of phosphorus oxychloride, and 30 ml of polyphosphoric acid in place of pyrophosphoric acid were used, to obtain 8.52 g of methyl 8-ferrocenoyl octanate represented by the formula (F) in a yield of 74.2%. The proton nuclear magnetic resonance ($^1$H—NMR) spectrum of the product is shown in FIG. 6. The result showed that the resulting product was the desired compound (methyl 8-ferrocenoyl octanoate).

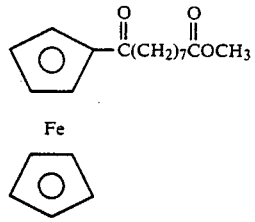

(F)

COMPARATIVE EXAMPLE 1

50 g of 11-bromoundecanoic acid was heat-refluxed with 90.0 of thionyl chloride for 2 hours. Then, unreacted thionyl chloride was distilled away, and the residue was vacuum-distilled, to obtain 11- bromoundecanoic acid chloride. Said product was stirred with 37.6 g of anhydrous aluminum chloride in methylene chloride so as not to be 5° C. or more, to obtain a methlene chloride solution.

Subsequently, 35.0 g of ferrocene was dissolved in methylene chloride in another vessel, cooled to 5° C., and the methylene chloride solution prepared above was dropped thereto so as not to be 5° C. or more, and then stirred for 3 hours.

After the completion of reaction, the reaction product was treated with dilute hydrochloric acid and purified with column chromatography, to obtain 56.9 g of 10-bromodecanylferrocenyl ketone represented by the formula (C) shown before, in a yield of 69.8%.

EXAMPLE 7

8.08 g of sebacic acid was added to 100 ml of 85% phosphoric acid and 100 g of polyphosphoric acid and heated at 180° C. for 3 hours, while the pressure was reduced with vacuum pump (1 mmHg).

After the resulting mixture was cooled, 1.86 g of ferrocene and 20 ml of methylene chloride were added, and heat-refluxed at 50° C. for 9 hours, then poured into water. The unreacted sebacic acid was filtrated off, the solution was separated with methylene chloride, and the organic layer was extracted, then reverse-extracted with aqueous alkali solution.

Further, said aqueous alkali solution layer was acidified, and extracted again with methylene chloride, to obtain the ferrocenoylnonanoic acid represented by the formula (G) in an amount of 3.51 g and in a yield of 95.%.

Figure 7:
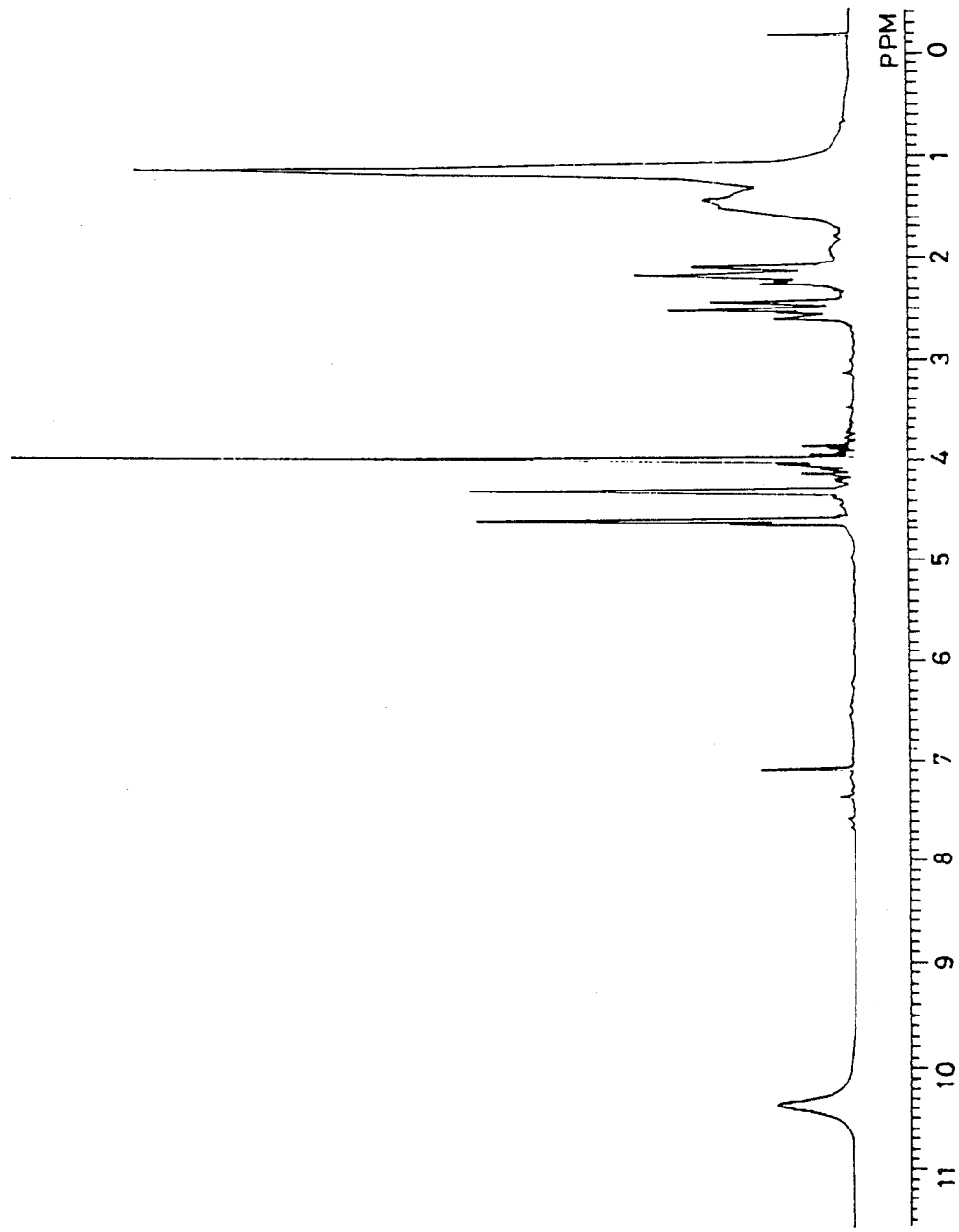

The proton nuclear magnetic resonance ($^1$H—NMR) spectrum of the product is shown in FIG. 7. The result showed that the product was the desired ferrocenoylnonanoic acid.

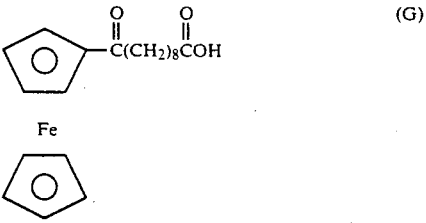

(G)

EXAMPLE 8

The procedure of Example 7 was repeated except that 100 ml of 99% phosphoric acid was used in place of 100 ml of 85% phosphoric acid, 11.46 g of hexadecanedicarboxylic acid was used in place of 8.08 g of sebacic acid, and that the pressure was not reduced, to obtain the ferrocenoylpentadecanoic acid represented by the formula (H) in an amount of 3.95 g and in a yield of 87.0%.

Figure 8:
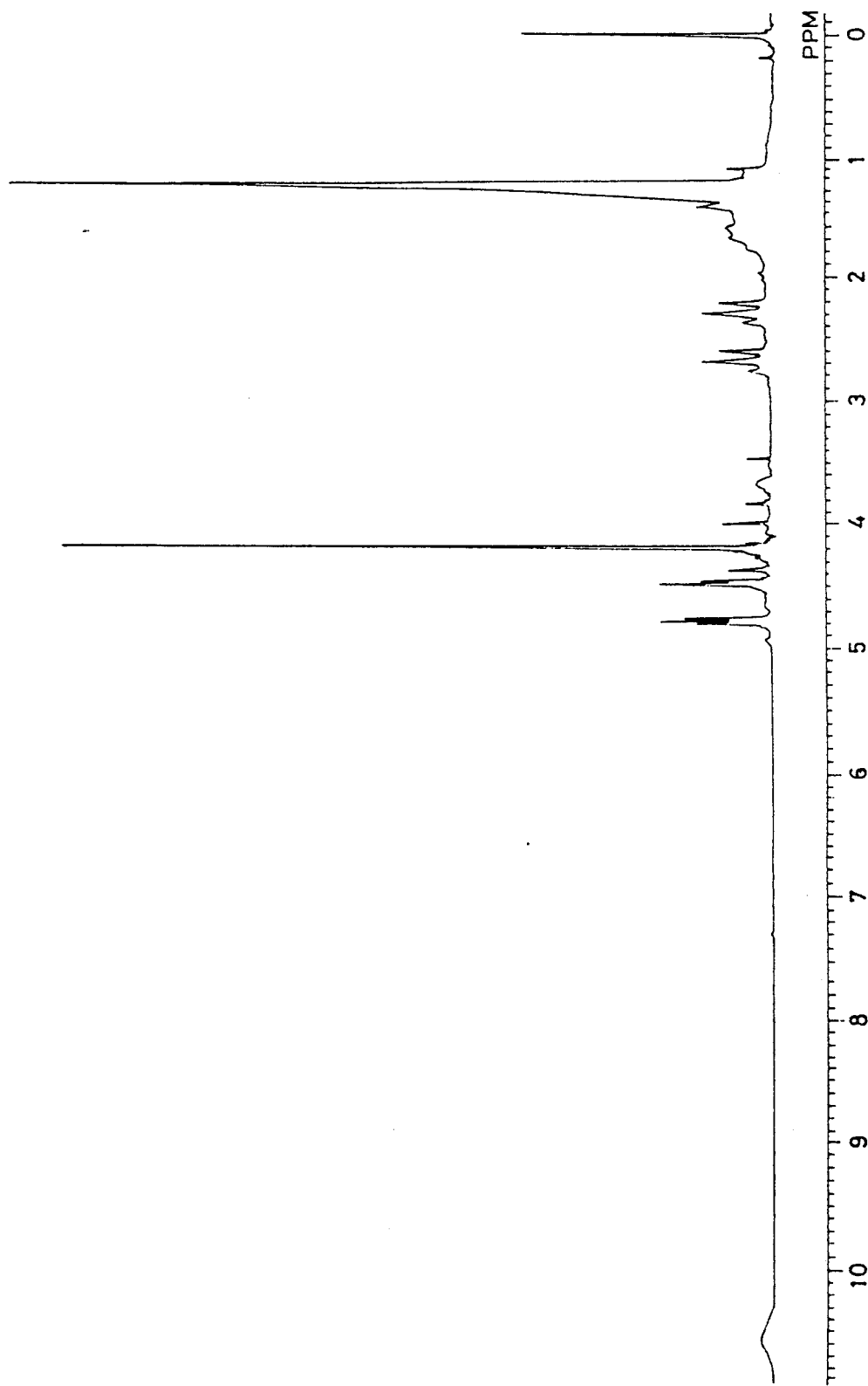

The proton nuclear magnetic resonance ($^1$H—NMR) spectrum of the product is shown in FIG. 8. The result confirmed that the resulting product was the desired ferrocenoylpentadecanoic acid.

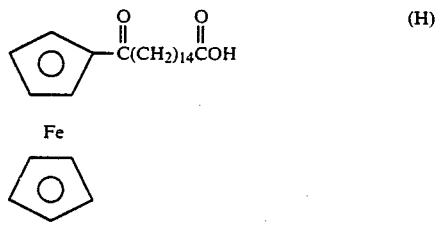

(H)

EXAMPLE 9

The procedure of Example 7 was repeated except that 100 ml of 85% phosphoric acid was not used, and 8,65 g of undecanedicarboxylic acid was used in place of 8.08 g of sebacic acid, and the pressure was not reduced, to obtain the ferrocenoyldecanoic acid represented by the formula (I) in an amount of 3.42 g and in a yield of 89.0%.

Figure 9:
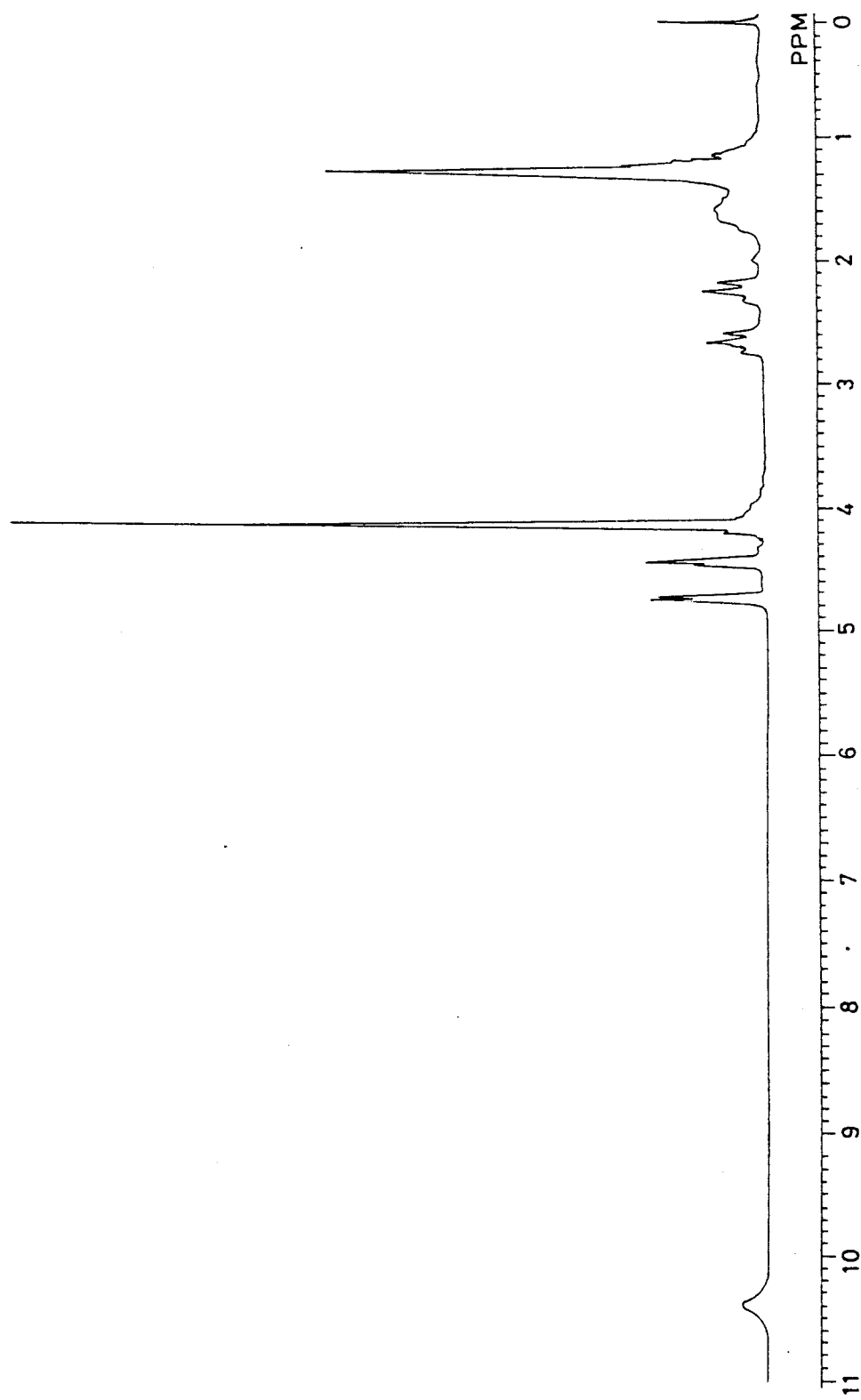

The proton nuclear magnetic resonance ($^1$H—NMR) spectrum of the product is shown in FIG. 9. The result confirmed that the resulting product was the desired ferrocenoyldecanoic acid.

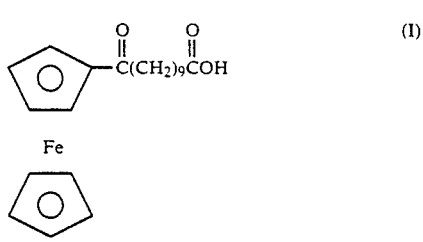

EXAMPLE 10

The procedure of Example 7 was repeated except that 100 g of pyrophosphoric acid was used in place of 100 ml of 85% phosphoric acid and 100 g of polyphosphoric acid, and that the pressure was not reduced, to obtain a ferrocenoylnonanoic acid in an amount of 2.41 g and in a yield of 65.0%.

Figure 10:
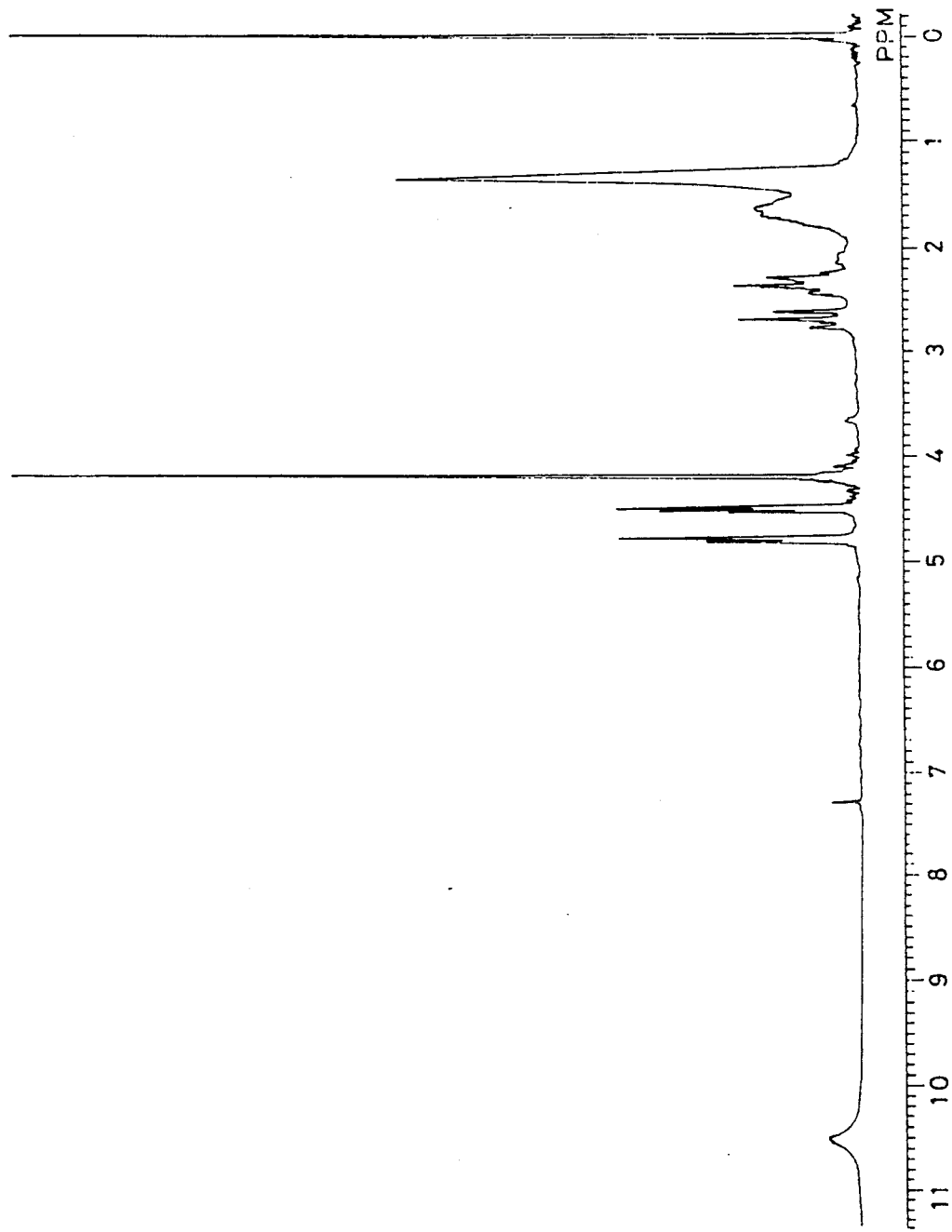

The proton nuclear magnetic resonance ($^1$H—NMR) spectrum of the product is shown in FIG. 10. The result confirmed that the resulting product was the desired ferrocenoylnonanoic acid.

EXAMPLE 11

The procedure of Example 7 was repeated except that 100 g of pyrophosphoric acid was used in place of 100 g of polyphosphoric acid, and 5.28 g of glutaric acid was used in place of 8.08 g of sebacic acid, to obtain the ferrocenoylbutyric acid represented by the forumla (J) in an amount of 2.16 g and in a yield of 72.0%.

Figure 11:
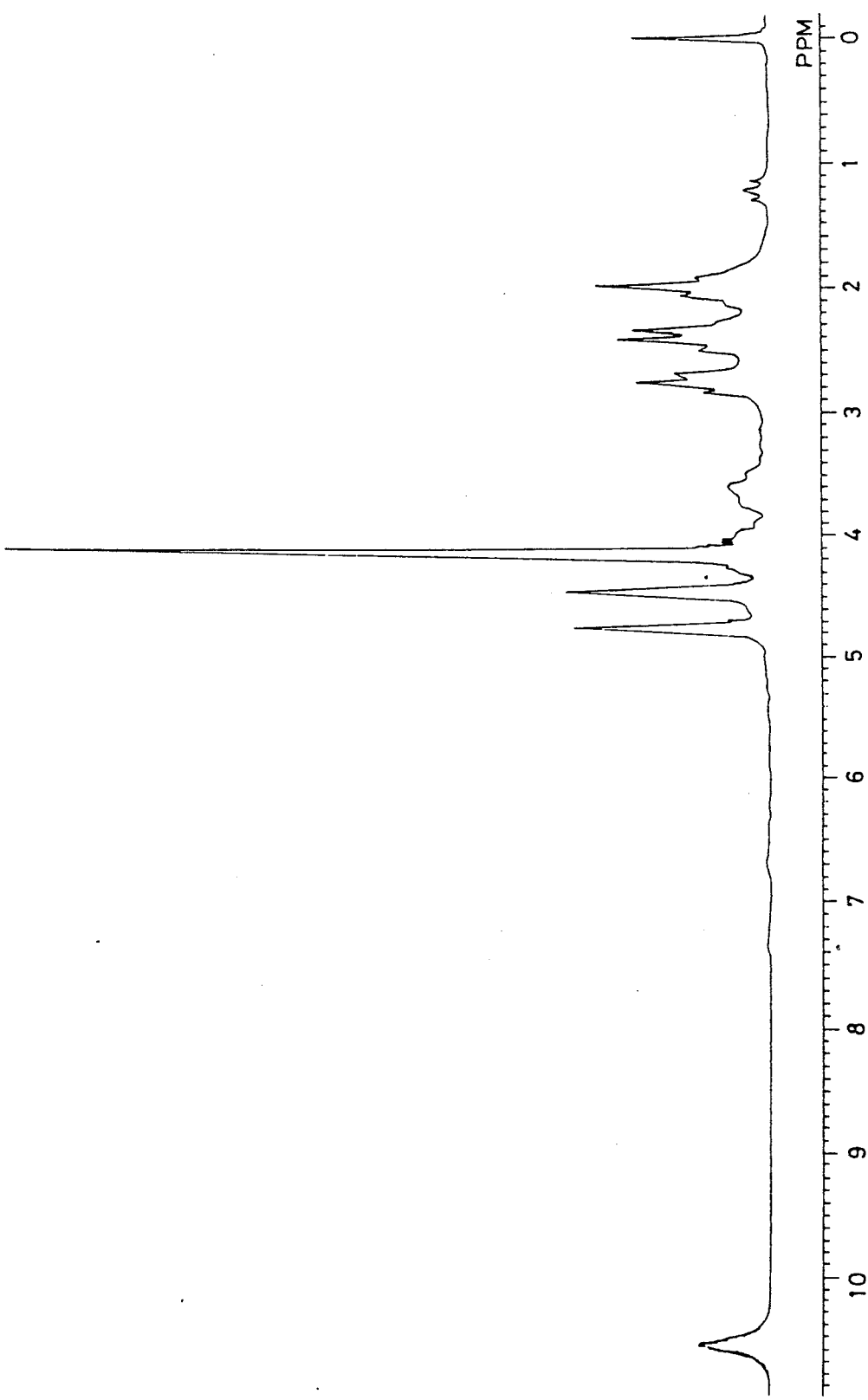

The proton nuclear magnetic resonance ($^1$H—NMR) spectrum of the product is shown in FIG. 11. The result confirmed that the resulting product was the desired ferrocenoylbutyric acid.

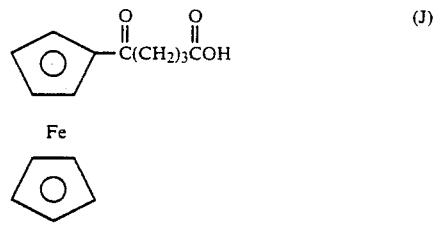

EXAMPLE 12

5.85 g of adipic acid, 1.86 g of ferrocene, 50 ml of pyrophosphoric acid and 20 ml of di n-butylether were added and stirred while heating at 60° C. to 70° C. for 3 hours, and then the same procedure as in Example 7 was conducted, to obtain the ferrocenylvaleric acid in an amount of 2.29 g and in a yield of 73.0%.

Figure 12:
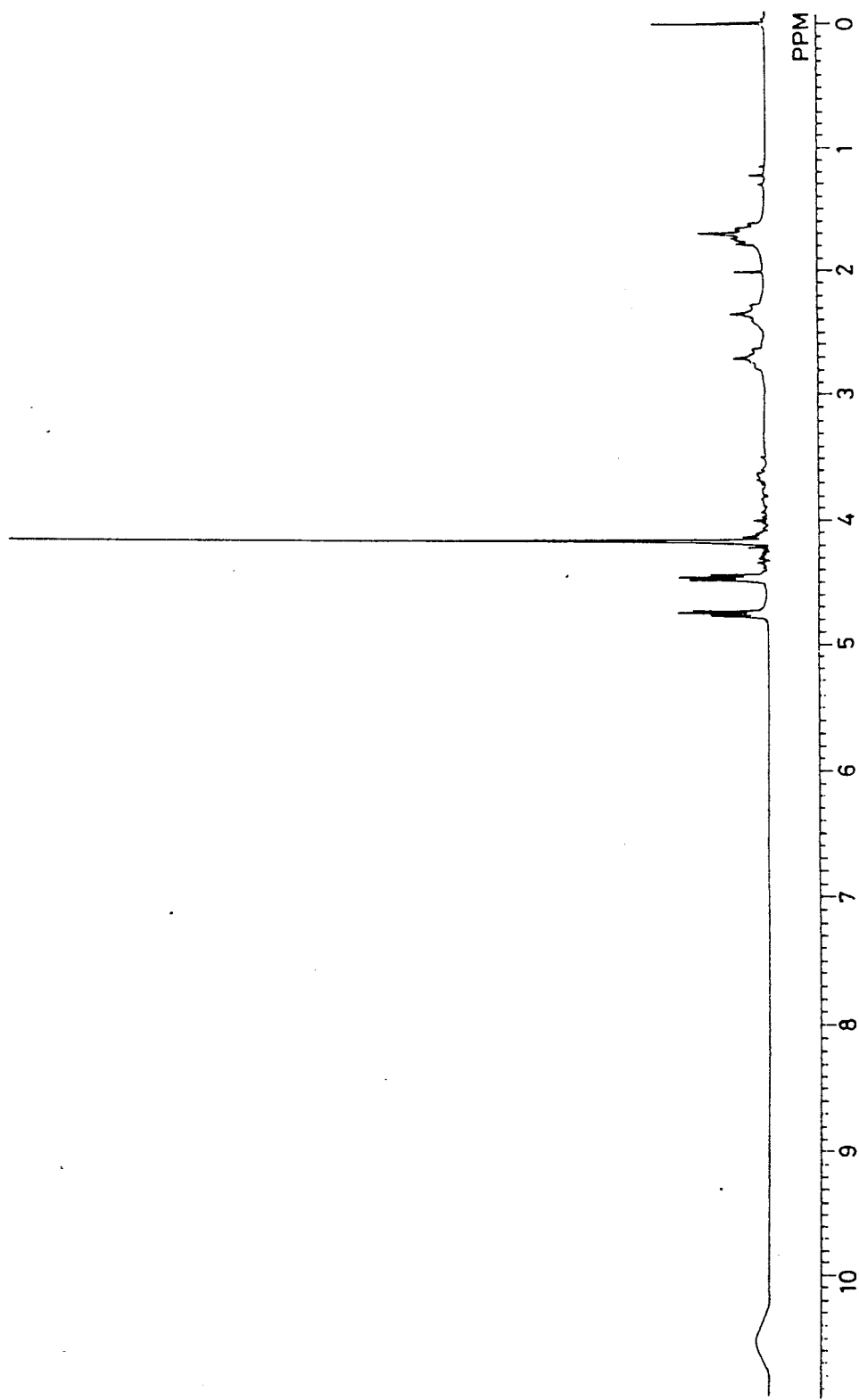

The proton nuclear magnetic resonance ($^1$H—NMR) spectrum of the product is shown in FIG. 12. The result confirmed that the resulting product is the desired ferrocenoylvaleric acid.

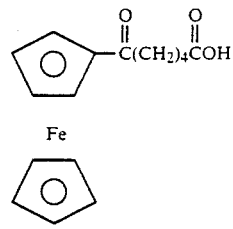

EXAMPLE 13

The procedure of Example 12 was repeated except that polyphosphoric acid was used in place of pyrophosphoric acid, and 8.08 g of sebacic acid was used in place of 5.85 g of adipic acid, to obtain ferrocenoylnonanoic acid in an amount of 3.41 g and in a yield of 92.0%.

Figure 13:
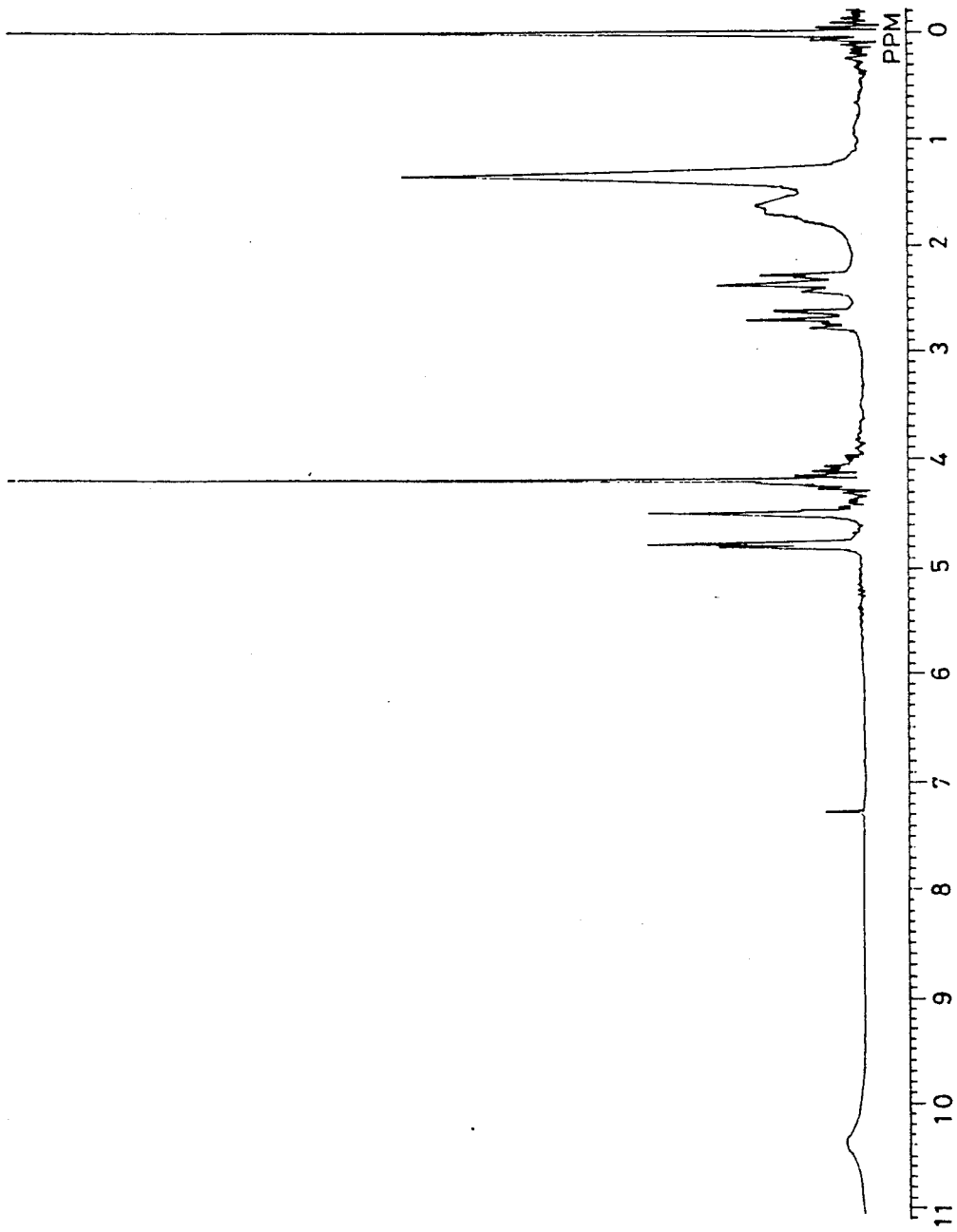

The proton nuclear magnetic resonance ($^1$H—NMR) spectrum of the product is shown in FIG. 13. The result confirmed that the resulting product was the desired ferrocenoylnonanoic acid.

EXAMPLE 14

0.67 g of sebacic acid, 1.0 ml of triethylamine and 2 ml of phosphorus oxychloride with 40 ml of methylene chloride were added and stirred at 0° C. for 30 minutes, and then 60 ml of pyrophosphoric acid and 6.0 g of ferrocene were added, and the resulting mixture was heat-refluxed. Subsequently, the same procedure as in Example 7 was conducted, to obtain a ferrocenoylnonanoic acid in an amount of 2.22 g and in a yield of 60.0%.

Figure 14:
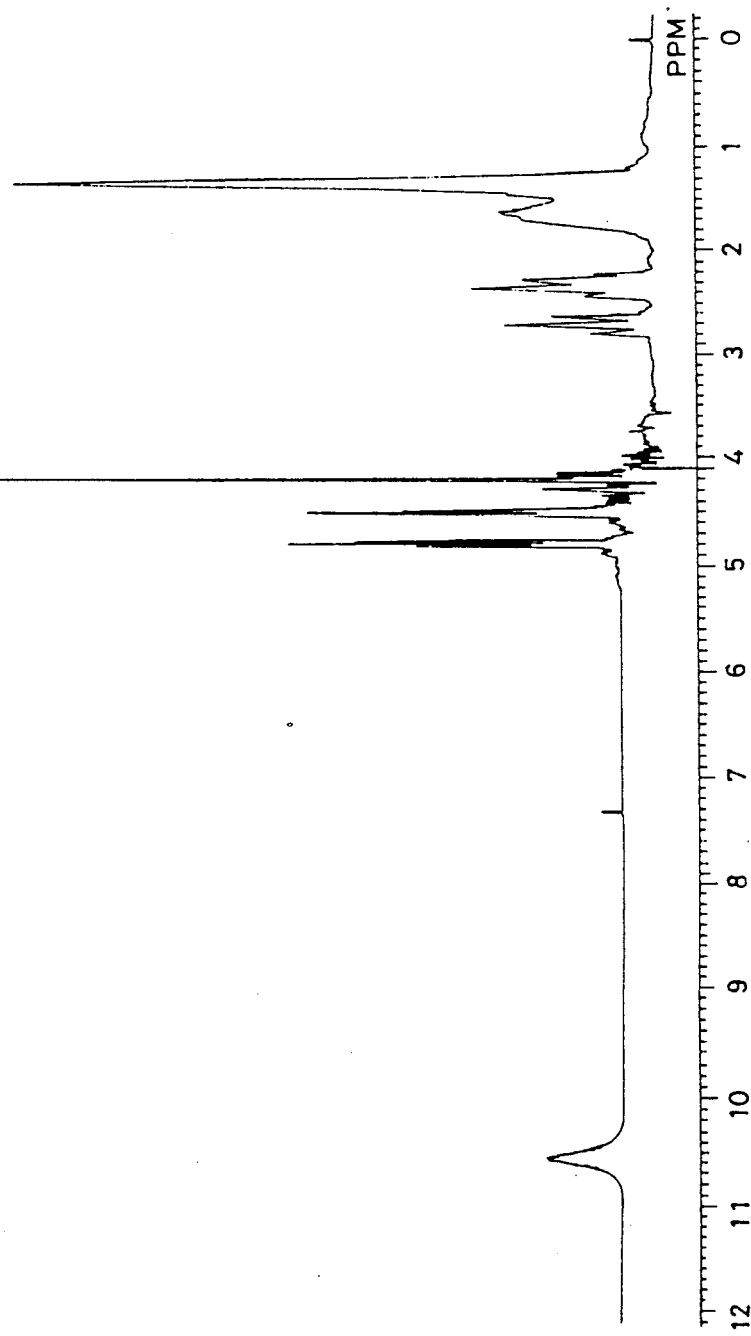

The proton nuclear magnetic resonance ($^1$H—NMR) spectrum of the product is shown in FIG. 14. The result confirmed that the resulting product was the desired ferrocenoylnonanoic acid.

EXAMPLE 15

The procedure of Example 14 was repeated except that 0.57 g of dimethyl chlorophosphate was used in place of 2 ml of phosphorus oxychloride, and 0.55 g of terephthalic acid was used in place of 0.67 g of sebacic acid, and 1.77 g of aluminum chloride was used in place of 60 ml of pyrophosphoric acid, to obtain the ferrocenoylbenzoic acid represented by the formula (L) in an amount of 0.58 g and in a yield of 52.3 %.

Figure 15:
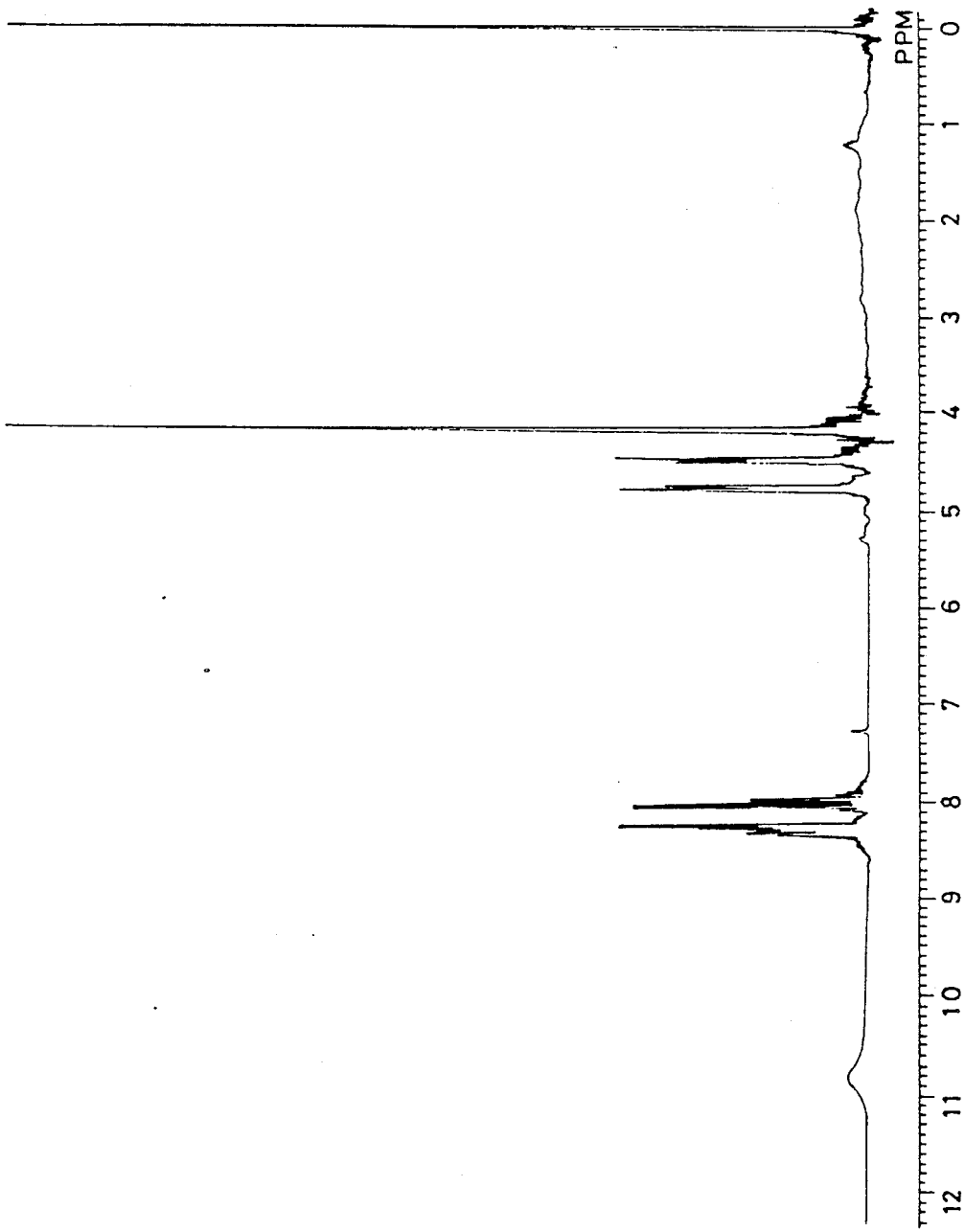

The proton nuclear magnetic resonance ($^1$H—NMR) spectrum of the product is shown in FIG. 15. The result confirmed that the resulting product was the desired ferrocenoylbenzoic acid.

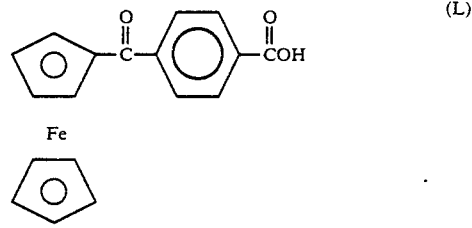

EXAMPLE 16

20 g of polyphosphoric acid, 40 g of pyrophosphoric acid, 1.86 g of ferrocene and 1.60 g of 3,3-dimethylglutaric acid were added and stirred at room temperature for 3 hours, then selfexothermic result was obtained, which made the reaction proceed. Subsequently, the same procedure as in Example 7 was conducted, to obtain a ferrocenoyl-3,3-dimethylbutyric acid represented by the formula (M) in an amount of 2.53 g and in a yield of 77.0%.

Figure 16:
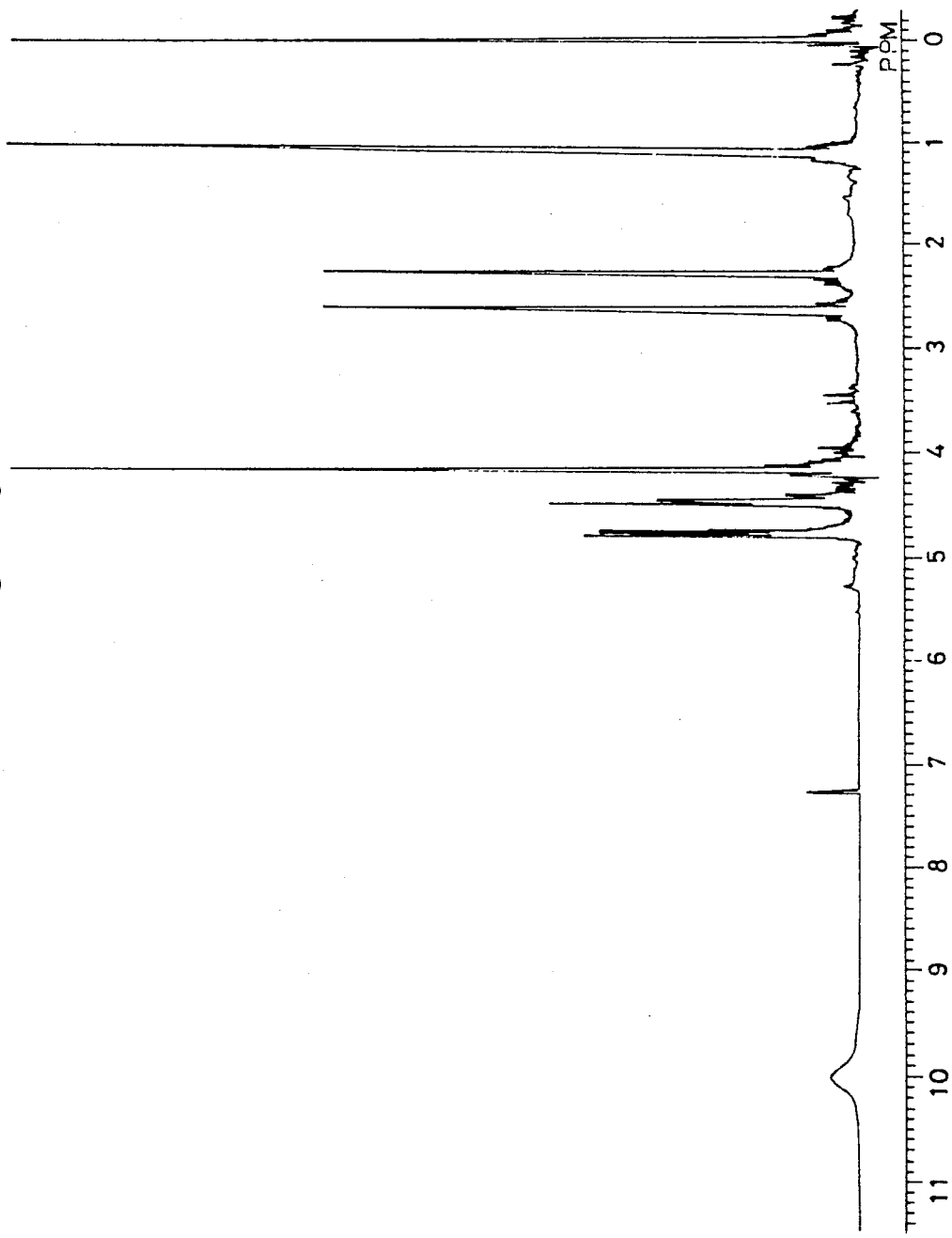

The proton nuclear magnetic resonance ($^1$H—NMR) spectrum of the product is shown in FIG. 16. The result confirmed that the resulting product was the desired ferrocenoyl-3,3-dimethylbutyric acid.

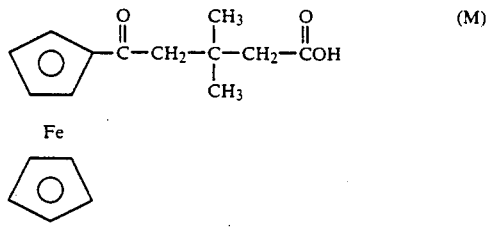

(M)

COMPARATIVE EXAMPLE 2

(1) 40.5 g of sebacic acid and 25.8 g of diethyl sebacate were stirred at 100° C. in di n-butylether in the presence of conc. hydrochloric acid for 5 hours while ethanol was added dropwise.

Subsequently, the mixture was poured into hexane, then the precipitated sebacic acid was removed, and subjected to extraction with aqueous alkali solution. The resulting extract was acidified, and extracted with ethyl acetate, and further concentrated, to obtain 9-ethoxycarbonylnonanoic acid in an amount of 23.4 g in a yield of 50.8%.

(2) 23.4 g of 9-ethoxycarbonylnonanoic acid obtained in (1) was heat-refluxed in 30 ml of thionyl chloride for 3 hours, and then vacuum-distilled, to obtain 19.3 g of 9-ethoxycarbonylnonanoic acid chloride in a yield of 76.2%.

(3) In the presence of 10.4 g of anhydrous aluminum chloride, 14.0 g of ferrocene and 19.3 g of 9-ethoxycarbonylnonanoic acid chloride obtained in (2) were reacted at room temperature in methylene chloride solvent.

Then, the reaction product was treated with dilute hydrochloric acid, and purified with silica gel column, to obtain 23.4 g of ethyl 9-ferrocenoylnonanate in a yield of 75.9%.

(4) 20.5 g of ethyl 9-ferrocenoylnonanate obtained in (3) was heat-refluxed in ethanol in the presence of 5.1 g of potassium hydroxide, to obtain 18.1 g of 9-ferroceniylnonanoic acid in a yield of 95%.

The total yield of (1) to (4) above was so small as 27.9%.

INDUSTRIAL APPLICABILITY

As described above, according to the process of the present invention, desired ferrocenoyl derivatives can be produced in a simple process and in a high yield.

Further, according to the process of the present invention, byproduct is inhibited from resulting, acyation reaction of ferrocene derivative proceeds selectively, and a ferrocenoyl derivative is produced in a high yield.

The ferrocenoyl derivatives obtained by the process of the present invention is very useful as the intermediate material in production of highly active functional materials such as functional polymers, LB films, surfactants, charge transfer complexes, ion sensors, masking agents, and coupling agents. Among all, micelle forming agent (surfactant) in so-called Micellar Disruption Method or the intermediate material thereof.

Accordingly, the process of the present invention has a very high value in practical use, as a process for industrial production of the ferrocenoyl derivatives having a high usefulness as described above.

We claim:

1. A process for producing ferrocenoyl derivative carboxylic acid, which comprises reacting a ferrocene derivative with a monocarboxylic acid or dicarboxylic acid in the presence of a catalyst.

2. The process according to claim 1 wherein the catalyst comprises phosphoric acid or a derivative thereof.

3. The process according to claim 1 wherein the ferrocene derivative is represented by the general formula:

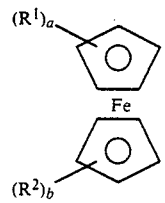

wherein $R^1$ and $R^2$ are each a hydrogen atom, a methyl group, a methoxyl group, a hydroxyl group, an amino group, a dimethylamino group or a halogen atom, a indicates an interger of 1 to 4, and b indicates an interger of 1 to 5.

4. The process according to claim 1 wherein the monocarboxylic acid is represented by the general formula:

$$\text{HOC(CH}_2)_m\text{X(CH}_2)_n\text{Y}$$

wherein X is

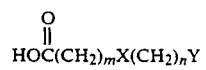

($R^3$ is a hydrogen atom, an an alkyl group having 1 to 5 carbon atoms, an alkoxyl group having 1 to 5 carbon atoms, a hydroxyl group, an amino group, a dimethylamino group, an alkoxycarbonyl group having 1 to 5 carbon atoms or a halogen atom, and a is as defined above),

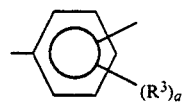

($R^3$ is as defined above),

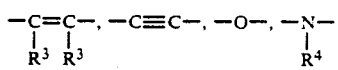

($R^4$ is a hydrogen atom or an alkyl group having 1 to 5 carbon atoms),

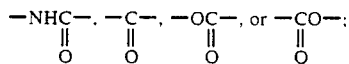

m and n are positive integers satisfying $m+n \geq 0$, and Y is a hydrogen atom, a halogen atom or a nitrile group.

5. The process according to claim 1 wherein the dicarboxylic acid is represented by the general formula:

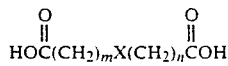

wherein X, m and n are as defined above.

6. The process according to claim 2 wherein the catalyst comprising phosphoric acid or derivative thereof is at least one compound selected from the group consisting of phosphoric acid, methaphosphoric acid, orthophoshporic acid, pyrophosphoric acid, polyphosphoric acid, phosphoric acid halide, and phosphorus halide.

* * * * *

UNITED STATES PATENT AND TRADEMARK OFFICE
CERTIFICATE OF CORRECTION

PATENT NO. : 5,110,964
DATED : May 5, 1992
INVENTOR(S) : HIROI et al

It is certified that error appears in the above-identified patent and that said Letters Patent is hereby corrected as shown below:

Column 12, line 51 (claim 4), delete "an" (second occurrence).

Column 13, line 9 (claim 4), before "m" (first occurrence) insert --and--.

Column 13, line 9 (claim 4), delete "positive".

Signed and Sealed this

Thirtieth Day of August, 1994

*Attest:*

BRUCE LEHMAN

*Attesting Officer*     *Commissioner of Patents and Trademarks*